US006555702B2

(12) United States Patent
Sriram et al.

(10) Patent No.: US 6,555,702 B2
(45) Date of Patent: *Apr. 29, 2003

(54) PROTEIN KINASE INHIBITOR

(75) Inventors: Subramaniam Sriram, Nashville, TN (US); John Bright, Nashville, TN (US); Bishwajit Nag, Fremont, CA (US); Somesh D. Sharma, Los Altos, CA (US)

(73) Assignee: Calyx Therapeutics, Inc., Hayward, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/054,971

(22) Filed: Apr. 3, 1998

(65) Prior Publication Data

US 2002/0115714 A1 Aug. 22, 2002

Related U.S. Application Data

(63) Continuation-in-part of application No. 08/825,662, filed on Apr. 3, 1997, now Pat. No. 5,854,285.

(51) Int. Cl.[7] ......................... A61K 31/21; C07C 255/09
(52) U.S. Cl. ..................... 558/401; 558/391; 558/392; 514/514; 514/523; 514/525
(58) Field of Search ................ 517/514, 523, 517/525; 558/391, 392, 401

(56) References Cited

U.S. PATENT DOCUMENTS

| | | | |
|---|---|---|---|
| 5,196,446 A | 3/1993 | Levitzki et al. | 514/415 |
| 5,217,999 A | 6/1993 | Levitzki et al. | 514/413 |
| 5,266,594 A | 11/1993 | Dawson et al. | 514/560 |
| 5,302,606 A | 4/1994 | Spada et al. | 514/357 |
| 5,376,487 A | * 12/1994 | Ueda | 430/59 |
| 5,385,915 A | 1/1995 | Buxbaum et al. | 514/813 |

FOREIGN PATENT DOCUMENTS

| | | |
|---|---|---|
| WO | WO 95/14464 | 6/1995 |
| WO | WO 95/21613 | 8/1995 |

OTHER PUBLICATIONS

Gazit et al., Tyrphostins I: Synthesis . . . , Journal of Medicinal Chemistry, v. 32, p. 2344–2352, 1989.*
Berge et al., Pharmaceutical Salts, Journal of Pharmaceutical Sciences, v.66, 1–19, 1974.*
Alexis Biochemicals, "Apoptosis, Cell Trafficking and Signal Transduction" Catalog, pp. 364–371, 1997/98.
Galea, E., et al. (1995) "Differential suppression of glial nitric oxide induction by structurally related tyrosine kinase inhibitors," *Neuroscience Lett.* 200:195–198.
Gazit et al., (1989) *J. Med. Chem.*, 32:2344–2352.
Gazit et al., (1991) *J. Med. Chem.*, 34:1896–1907.
Gazit et al., (1993) *J. Med. Chem.*, 36:3556–3564.
Katsumi, I., et al. (1985) *Chem Pharm. Bull.* "Studies on Styrene Derivatives.II. Synthesis and Antiinflammatory Activity of 3,5–Di–tert–butyl–4–hydroxystyrenes," 34:1619–1627.
Kengatharan, M., et al. (1996) *Brit. J. of Pharm.* "Analysis of the signal transduction in the induction of nitric oxide synthase by lipoteichoic acid in macrophages," 117:1163–1170.
Levitzki, A. (1992) "Tyrophostins: tyrosine kinase blockers as novel antiproliferative agents and dissector of signal transduction," *The FASEB Journal* 6:3275–3282.
Novogrodsky, A., et al. (1994) "Prevention of Lipopolysaccharide–Induced Lethal Toxicity by Tyrosine Kinase Inhibitors," *Science* 264:1319–1322.
Shiraishi, T., et al. (1987) "Specific Inhibitors of Tyrosine–Specific Protein Kinase. I. Synthesis and Inhibitory Activities of α–Cyanocinnamamides," *Chem. Pharm. Bull.* 36:974–981.
Tan, C.M., et al. (1995) "Oxidant Stress Enhances Adenylyl Cyclase Activation," *Circulation Research* 77:710–717.
Vanichkin, A., et al. (1996) "Late Administration of a Lipophilic Tyrosine Kinase Inhibitor Prevents Lipopolysaccharide and *Escherichia coli*–Induced Lethal Toxicity," *J. Infectious Diseases* 173:927–933.
Levitzki et al., "SSI tyrphostin pharmaceuticals," *Database Caplus on STN*, AN 1995: 782006, WO 9514464 A1, Sep. 20, 1991.
Salari, "Tyrphostins for treatment of allergic, inflammatory and cardiovascular diseases," *Database Caplus on STN*, AN 1992: 420509, CA 2012634 AA, Sep. 20, 1991.

* cited by examiner

*Primary Examiner*—Bennett Celsa
(74) *Attorney, Agent, or Firm*—Pillsbury Winthrop LLP

(57) ABSTRACT

A compound of the formula I:

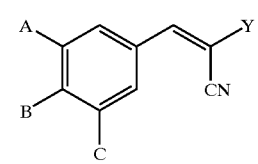

wherein A and C are independently H, alkyl of 1–6 carbon atoms, hydroxy, or alkoxy of 1–6 carbon atoms;

B is hydroxy, alkoxy of 1–6 carbon atoms —$CO_2Z$, —$O(CH_2)_mCO_2Z$, —$SO_3Z$, —$OPO_3Z_2$; and Y is cyano,

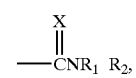

—$C(NR_1R_2)=C(CN)_2$;

wherein X=O or S, and $R_1$ and $R_2$ are independently H, benzyl, —$CH(CH_3)C_6H_6$,
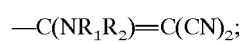 , phenyl; —$CO_2R$;
n=2–4; R is lower alkyl of 1–6 carbon atoms;

m=1–4 and Z is H, a cation or lower alkyl of 1–6 cabon atoms; is used for treating inflammation, immunological diseases or diabetes.

10 Claims, 5 Drawing Sheets

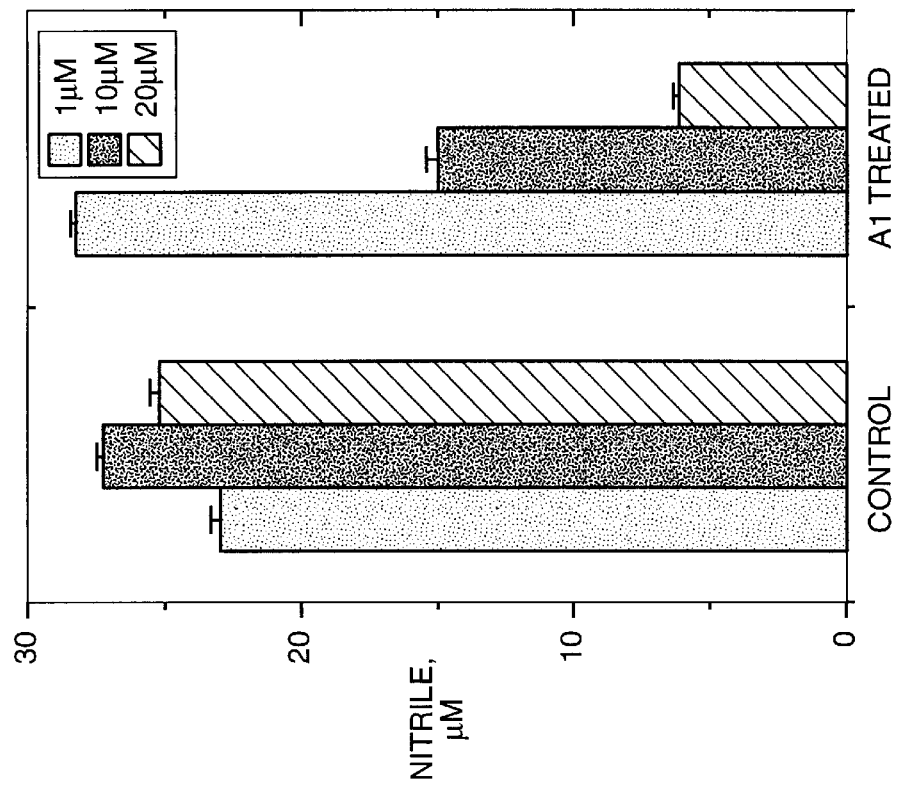
FIG._1B
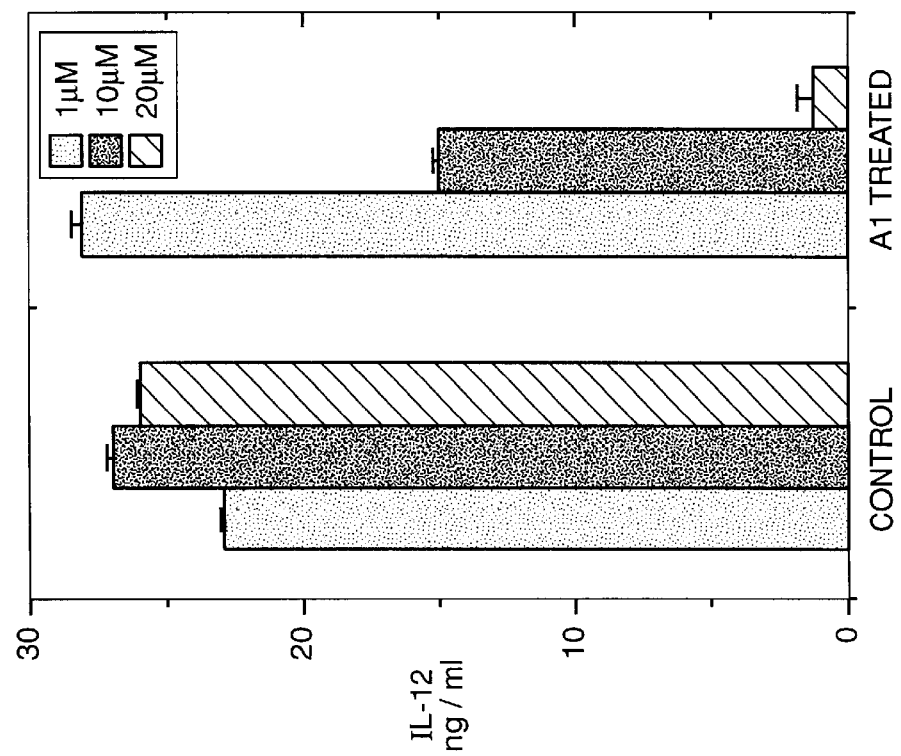
FIG._1A

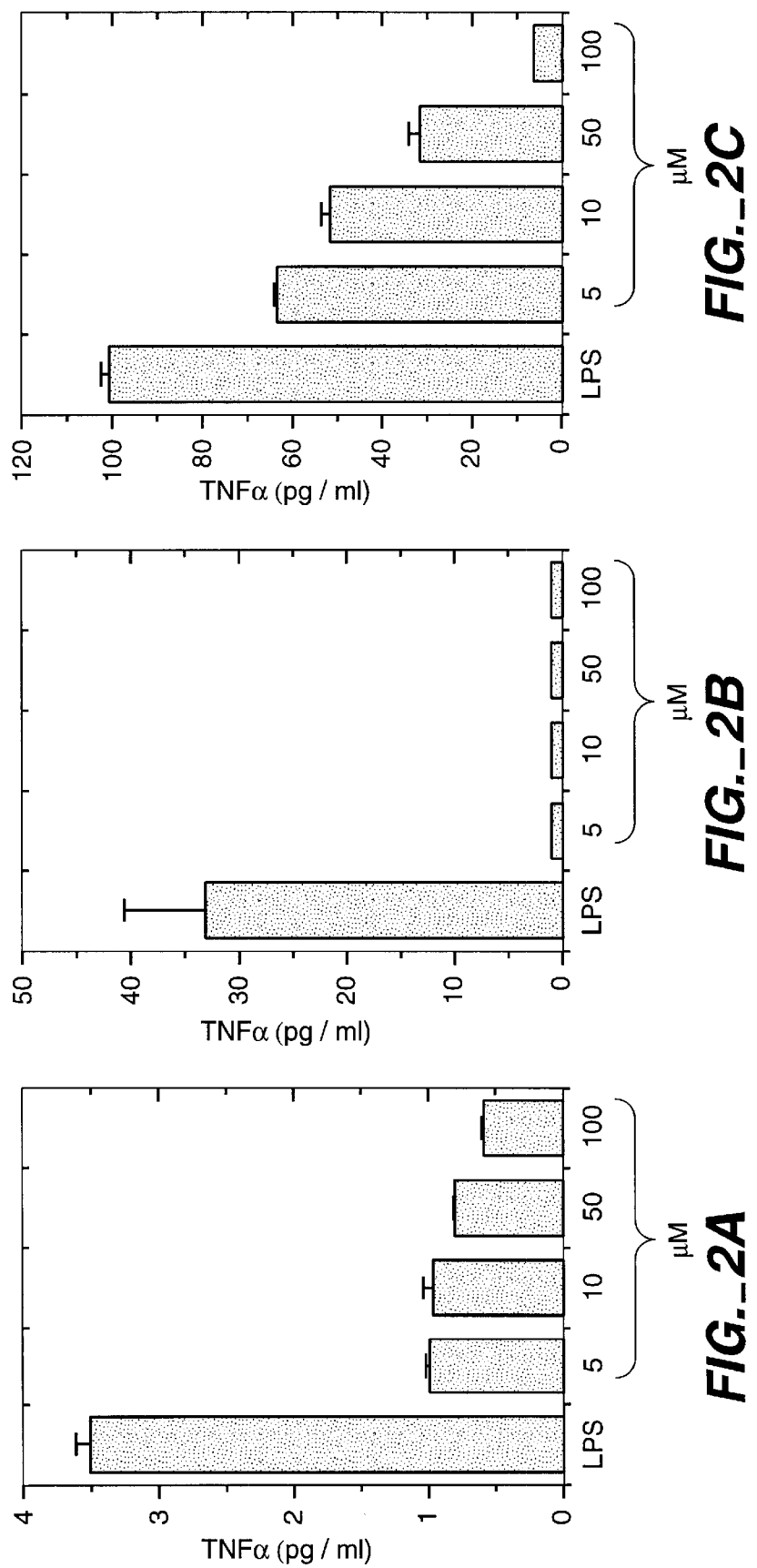

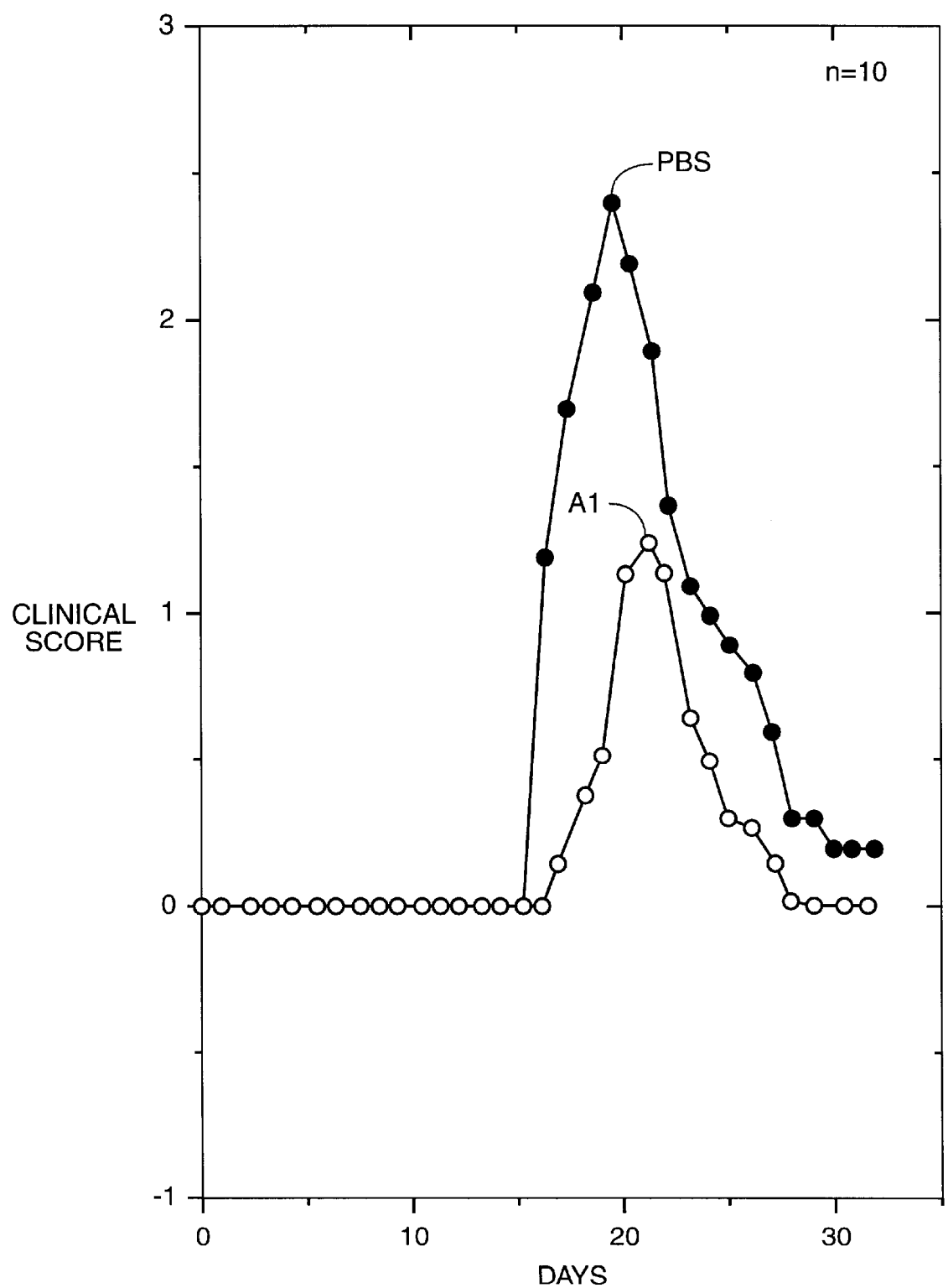
FIG._3

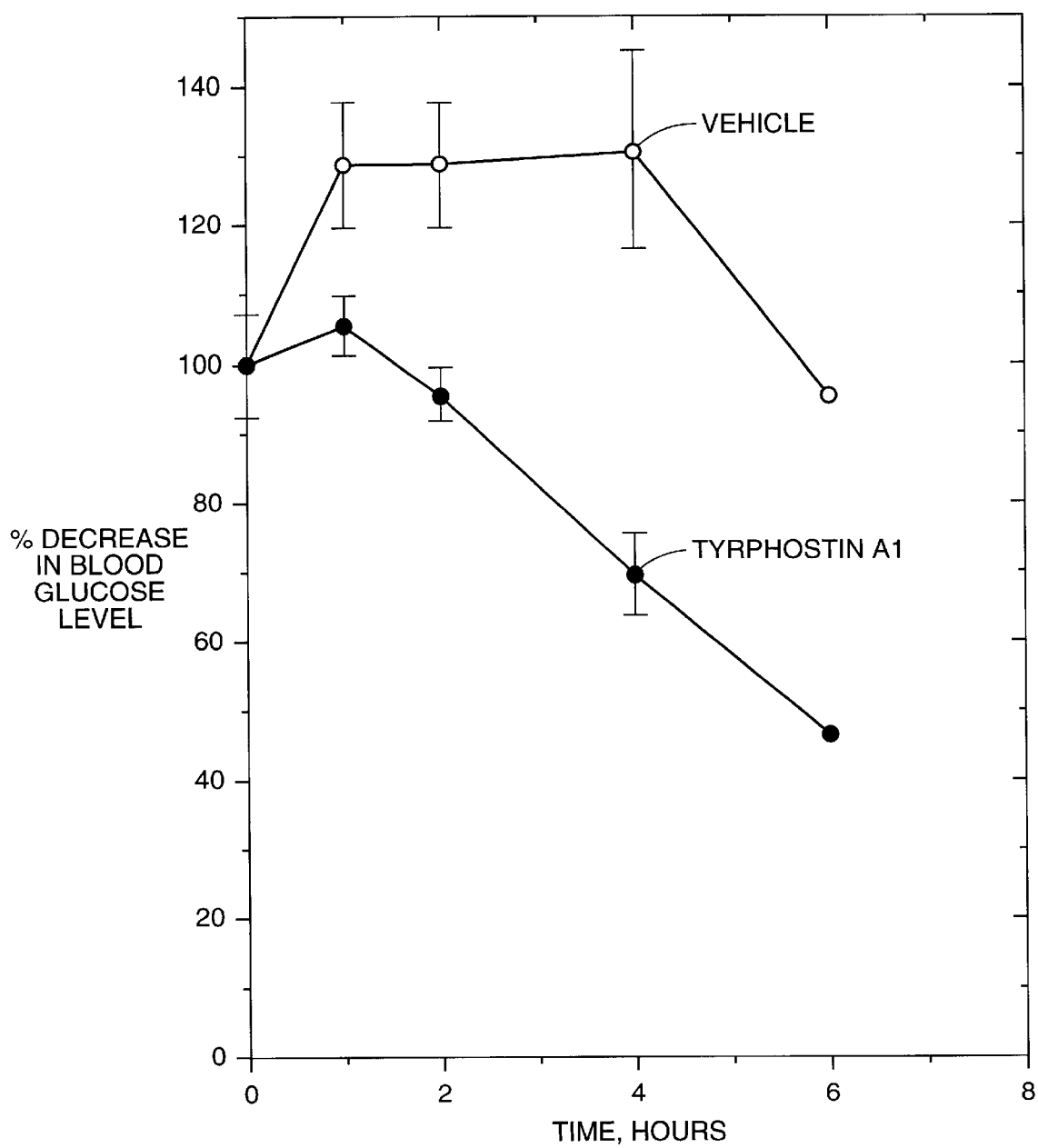
FIG._4

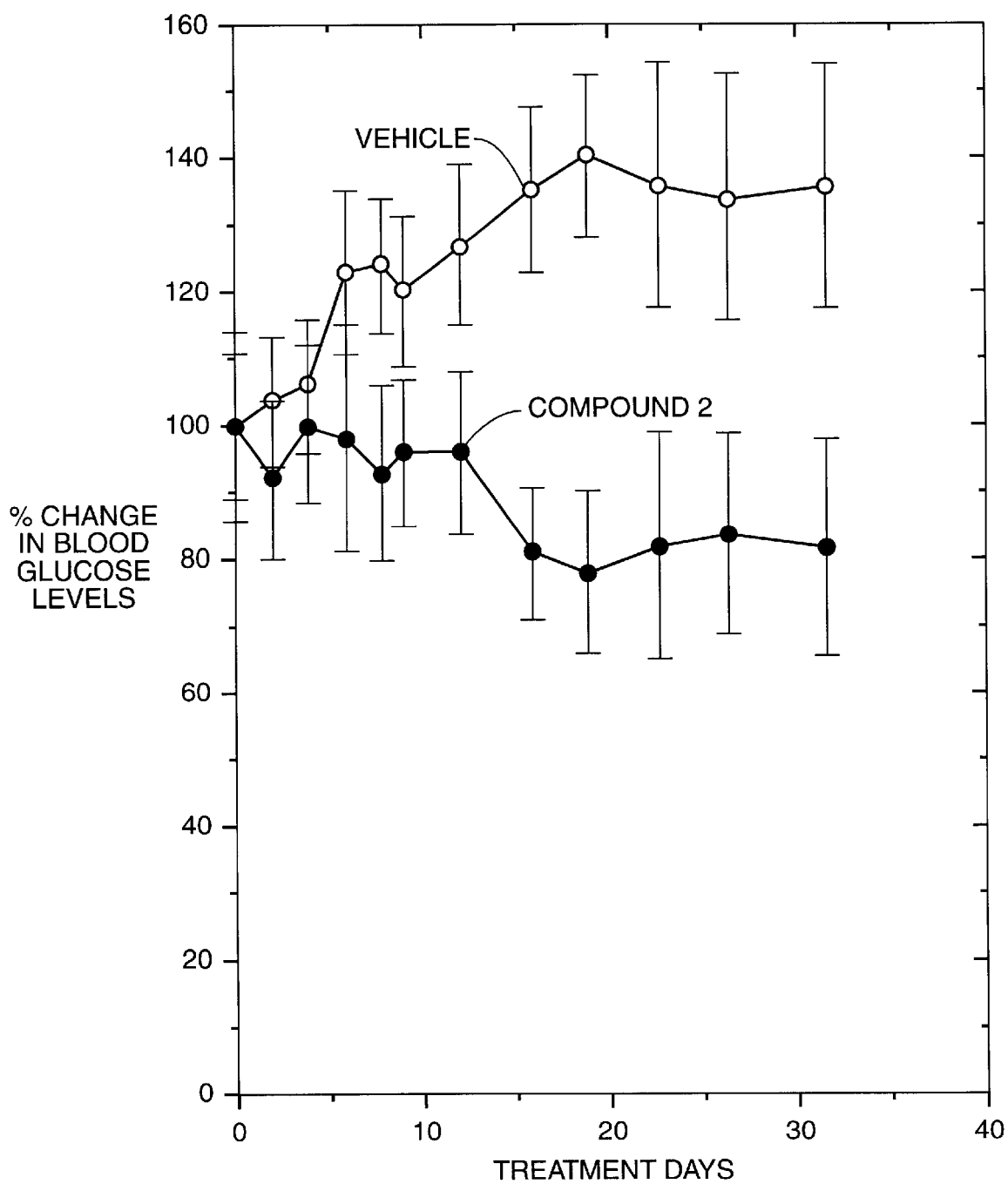
FIG._5

PROTEIN KINASE INHIBITOR

CROSS-REFERENCE TO RELATED APPLICATION

This is a continuation-in-part of U.S. application Ser. No. 08/825,662, filed Apr. 3, 1997, now U.S. Pat. No. 5,854,285.

FIELD OF THE INVENTION

The present invention relates to the method of use of styrene derivatives to treat inflammation, immunological diseases, or diabetes.

BACKGROUND OF THE INVENTION

The present invention is based on the crucial role played by signaling pathways in affecting the function of cytokines. Cytokines are molecules secreted by immune cells and are important in mediating immune responses. Cytokines effect their functions at the site of secretion or at distant sites. Cytokines initiate their responses by binding to their respective receptors. This receptor-ligand interaction induces a signal and leads to the transcription of new genes that change the functional capacity of the target cell. Thus the effect of cytokines may result in the secretion of other cytokines, altered cellular function, cell division or differentiation. In most immune cells (T, B and macrophages) cytokine receptors themselves act as protein tyrosine kinases that are phosphorylated upon ligation of the receptor or are closely linked to phosphotyrosine kinases (PTK's).

Inhibitors of PTK function are known, such as querestin, the first one which was isolated. Querestin was found to inhibit not only PTK's but other enzymes such as cAMP dependent kinase, protein kinase C (PKC) and ATP requiring enzymes. Other naturally occurring compounds such as erbastatin, herbamycin and levandestin affect predominantly the function of PTK's and have been termed tyrphostins. Most tyrphostins are 100–1000 fold more potent in inhibiting PTK's than PKA, PKC or other calcium dependent kinases. So far the role of tyrphostins has focused on their potential application in neoplastic diseases. A recent therapeutic test of tyrphostins has been in the treatment of acute lymphoblastic leukemia, in which a known JAK2 kinase inhibitor was shown to inhibit the proliferation of leukemic cells without affecting mitogen-induced T cell proliferation.

The present invention is directed to treatment of immunological diseases or inflammation. The principal elements of the immune system are macrophages or antigen-presenting cells, T cells and B cells. The role of other immune cells such as NK cells, basophils, mast cells and dendritic cells are known, but their role in primary immunologic disorders is uncertain. Macrophages are important mediators of both inflammation and providing the necessary "help" for T cell stimulation and proliferation. Most importantly macrophages make IL 1, IL 12 and TNFα all of which are potent pro-inflammatory molecules and also provide help for T cells. In addition, activation of macrophages results in the induction of enzymes, such as cyclooxygenase II (COX II), nitric oxide (NO) and other free radicals capable of damaging normal cells. Many factors activate macrophages, including bacterial products, superantigens and interferon gamma (IFNγ). It is believed that PTK's and other undefined cellular kinases are involved in the activation process.

Macrophages take up and break down antigens into small fragments. These fragments then associated with the major histocompatibility complex II (MHC II). This complex of antigen fragments and MHC II is recognized by the T cell receptor. In association with appropriate co-stimulatory signals this receptor-ligand interaction leads to the activation and proliferation of T cells. Depending on the route of administration of antigen, their dose and the conditions under which macrophages are activated, the immune response can result in either B cell help and antibody production or on the development of cell mediated response. Since macrophages are sentinel to the development of an immune response, agents that modify their function specifically their cytokine secretion profile are likely to determine the direction and potency of the immune response.

SUMMARY OF THE INVENTION

This invention is directed to a method of treating immunological diseases, inflammation, or Type I and Type II diabetes with compounds of formula I shown below. The compounds inhibit the secretion of pro-inflammatory cytokines and thus prevent the development or inhibit established inflammatory responses.

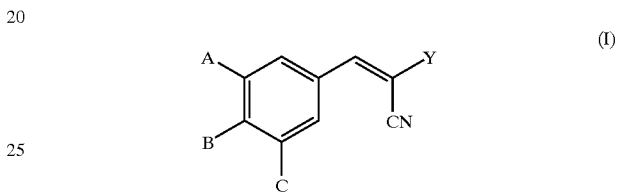

(I)

wherein A and C are independently H, alkyl of 1–6 carbon atoms, hydroxy, or alkoxy of 1–6 carbon atoms;

B is hydroxy, alkoxy of 1–6 carbon atoms, —$CO_2Z$, $O(CH_2)_mCO_2Z$, —$SO_3Z$, —$OPO_3Z_2$; and Y is cyano,

or

—$C(NR_1 R_2)$=$C(CN)_2$;

wherein X=O or S, and $R_1$ and $R_2$ are independently H, benzyl, —$CH(CH_3)C_6H_6$, —$(CH_2)_n C_6H_6$, phenyl; —$CO_2R$; n=2–4; R is lower alkyl of 1–6 carbon atoms; m=1–4 and Z is H, a cation or lower alkyl of 1–6 carbon atoms.

BRIEF DESCRIPTION OF THE DRAWING

FIG. 1A shows and FIG. 1B shows a the IL-12 and nitric oxide inhibition of tyrphostin 1A described in Example 1.

The TNFα production by tyrphostin A1 in three macrophage cell populations is shown for ANA-1 cells (FIG. 2A), peritoneal macrophage cells (FIG. 2B) and splenic macrophage cells (FIG. 2C).

FIG. 3 shows the prevention of EAE in mice by tyrphostin A1.

FIG. 4 shows the lowering of blood glucose by tyrphostin A1 in diabetic rats.

FIG. 5 shows the hypoglycemic effect of the sodium salt of 1-cyano-3-(4-carboxy-phenyl)-acrylonitrile in NOD mice.

DESCRIPTION OF THE PREFERRED EMBODIMENTS

As used herein the term tyrphostins is intended to denote a family of organic molecules that have the effect of inhibiting protein tyrosine kinases.

The immune diseases include those mediated by signaling pathways linked to pro-inflammatory cytokines, such as, multiple sclerosis, rheumatoid arthritis, contact and atopic dermatitis.

The compounds used in accordance with the present invention are those of the formula I. The alkyl and alkoxy groups in formula I may be linear or branched. A preferred class of compounds is that in which A and C are independently hydrogen or hydroxy and Y is cyano. A particularly preferred subclass of novel compounds within this class are those compounds in which B is hydroxy, —$CO_2Z$, —$O(CH_2)_mCO_2Z$, —$SO_3Z$, —$OPO_3Z_2$; and A and C are both hydrogen.

Species within this preferred subclass include and the compounds of the formulas 2 through 7 shown in Table A.

1993 to Levitski et al., all of which are incorporated by reference herein in their entirety.

The compounds may be administered to the host suffering from inflammation, an immunological disease or diabetes using any convenient administration technique, where such techniques include intravenous, intradermal, intramuscular, subcutaneous, oral, and the like. The dosage delivered to the host will necessarily depend on the route by which the active compound is administered, but will generally range from about 1 to 500 mg/70 kg human body weight/day.

The compounds of this invention may be used in formulations using acceptable pharmaceutical vehicles for enteral, or parenteral, administration, such as, for example, water, alcohol, gelatin, gum arabic, lactose, amylase, magnesium stearate, talc, vegetable oils, polyalkylene glycol, and the like. The compounds can be formulated in solid form, e.g.,

TABLE A

| | Structure | SOLUBILITY |
|---|---|---|
| Tyrphostine 1A | $H_3CO$-C$_6H_4$-CH=C(CN)$_2$ | Chloroform<br>Ethanol (slightly)<br>vegetable oil (warm) |
| 2 | $NaO_2C$-C$_6H_4$-CH=C(CN)$_2$ | Water |
| 3 | (HO)(OH/HNEt$_3$ (~33%))P(=O)-O-C$_6H_4$-CH=C(CN)$_2$ | Water |
| 4 | (SO$_3$Na)(NaO$_3$S)-C$_6H_3$-CH=C(CN)$_2$ | Water |
| 5 | $NaO_2C$-CH$_2$-O-C$_6H_4$-CH=C(CN)$_2$ | Water |
| 6 | $EtO_2C$-CH$_2$-O-C$_6H_4$-CH=C(CN)$_2$ | Chloroform<br>Ethanol (warm) |
| 7 | HO-C$_6H_4$-CH=C(CN)$_2$ | Ethanol<br>Acetone |

The water-soluble compounds 2 through 5 are particularly useful since they are readily used in pharmaceutical formulations.

The compounds of the formula I are obtained by synthetic methods known in the art. See Gazit et al., *J. Med. Chem.,* 1991, 34:1896–1907; 1989, 32:2344–2352; 1993, 36:3556–3564; and U.S. Pat. No. 5,217,999, issued Jun. 8, as tablets, capsules, drages and suppositories, or in the liquid form, e.g., solutions, suspensions and emulsions. The preparations may also be delivered transdermally or by topical application.

The following examples are presented by way of illustration, and are not intended to limit the invention in any way.

EXAMPLE 1

Tyrphostin A1 (Formula I: A and C are H, B is methoxy, Y is CN) is as efficient as A10 (A is H, B is —NO$_2$, C is OH, Y is —CN) and B42 (A and B are OH, C is H, Y is C(O)NHCH$_2$C$_6$H$_6$) in inhibiting nitric oxide and IL 12 Secretion by splenic macrophages.

Tyrphostin A1 has been used as a negative control for tyrphostins because of it weak effect on inhibition of epidermal growth factor receptor (EGFR) kinase activity. Tyrphostin A10 has been shown to be protective in septic shock and B42 is effective in preventing the growth of leukemic cells in acute lymphoblastic leukemia.

The effects of these three tyrphostins on the secretion of pro-inflammatory cytokines from macrophages were compared. Mouse splenic macrophages were stimulated with 5 ugh/ml lipopolysaccharide (LPS) and treated with varying doses of tyrphostins. The cells were cultured for 72 hr and the amount of IL 12 and nitric oxide was measured. Tyrphostins A1, A10 and B42 all inhibited IL 12 production. In general, tyrphostin A1 was more potent (FIG. 1A) than the other tyrphostins in inhibiting IL 12 secretion. Similar results were obtained with respect to nitric oxide levels, with tyrphostin A1 (FIG. 1B) showing good results.

The effect of tyrphostin A1 on inhibition of TNFα was examined in vitro in a cultured macrophage cell line, peritoneal macrophages and splenic macrophages. Cells were cultured with 5 ug/ml LPS in the presence of varying concentrations of tyrphostin A1. Following 24 hr incubation, cell supernatants were harvested and the amount of TNFα was measured using a biological assay. Tyrphostin A1 inhibits TNFα secretion in three different populations (ANA-1, FIG. 2A; peritoneal macrophage cells, FIG. 2B; splenic macrophages cells, FIG. 2C) of macrophages. FIGS. 2A and 2C show that the inhibition occurs in a dose dependent fashion.

Tyrphostin A1 was also tested for its ability to modulate the function of cyclooxygenase (COX II), an enzyme found in cells in inflammatory lesions. Hence, down regulation of this enzyme will be highly beneficial in damping inflammation. The induction of COX II in murine peritoneal macrophages activated with LPS was inhibited by tyrphostin A1.

The restrictive effects of tyrphostin A1 on proinflammatory cytokines was confirmed by examining the enhanced expression of class II MHC molecules induced by IFNγ. Tyrphostin A1 at concentrations at which it inhibits secretion of pro-inflammatory cytokines had no effect on enhancement of class II MHC levels by IFNγ (Table I).

TABLE I

| Stimulation | % MHC Class II + Cells |
| --- | --- |
| None | 26.6% |
| IFNγ | 58.2% |
| IFNγ + Tyrphostin A1 (1 µM) | 64.1% |
| IFNγ + Tyrphostin A1 (10 µM) | 60.4% |

The selectivity of tyrphostins for macrophages was further confirmed by testing their effects on T cell proliferation induced by either IL 12 or IL 2. Mitogen stimulated mouse splenic T cells were cultured in serum free medium for 24 hr. The cells were then stimulated with either 1 U/ml IL 2 or 10 U/ml IL 12 in the presence or absence of tyrphostin A1. Tyrphostin B42 inhibited T cell proliferation when cultured with IL 2 or IL 12. Tyrphostin A1 and A10 did not show any significant inhibition.

EXAMPLE 2

Tyrphostin A1 is tested on experimental allergic encephalomyelitis (EAE) in mice.

The condition EAE is an animal model which mimics human multiple sclerosis. Therefore, the clinical efficacy of tyrphostin A1 was tested in mice suffering from EAE. Female SJL/J mice were randomly assigned into 2 groups of 5 animals each. EAE was induced by subcutaneous immunization with mouse spinal cord homogenate (800 ug/animal) in complete Freund's adjuvant on days 0 and 7. One group of animals was treated with 5 mg/kg tyrphostin A1 subcutaneously on days 1, 3, 5, 7 and 9 after immunization. Animals were observed and graded for the clinical signs every day. The severity of the disease was scored as: 1, loss of tail tone; 2' hind limb weakness; 3, hind limb paralysis; 4, moribund and 5, death.

FIG. 3 shows the summary of data on subcutaneous administration of tyrphostin A1 indicating a decrease in the clinical severity of EAE. Animals in the control group had a peak mean severity of 2.5 at day 20. This was reduced to 1.25 at day 20 by tyrphostin A1.

The data demonstrate the utility of tyrphostin A1 in blocking pro-inflammatory cytokines and in treating a prototype inflammatory disease.

EXAMPLE 3

FIG. 4 represents the hypoglycemic activity of Tryphostin A1 in streptozotocin-induced diabetic rats. Streptozotocin at a dose of 40 mg/kg body weight was injected in SD rats of average 200 g. Treatment of diabetic rats (average blood glucose 312 mg/dl) with a dose of 2 mg/kg body weight lowered the blood glucose level by 50%.

EXAMPLE 4

The hypoglycemic effect of Compound 2 (water-soluble analog of A1) was evaluated in the treatment mode in non-obese diabetic (NOD) mice. As shown in FIG. 5, daily oral administration in NOD mice has significant effect on blood glucose level as compared to vehicle treated animals.

These results demonstrate the use of tyrphostin A1 and its analog (Compound 2) in lowering blood glucose level and their use for the treatment of diabetes.

EXAMPLE 5

Preparation of Sodium 1-cyano-3-(4-carboxy-phenyl)-acrylonitrile

4-Carboxy benzaldehyde (3g), malononitrile (1.45g), anhydrous ethyl alcohol (20 ml) and of piperidine (5 drops) were mixed in a 100 ml round bottom flask. The resulting suspension was heated to reflux for 2.5 hr. The mixture was then allowed to attain ambient temperature and the separated solid was triturated with ethanol (20 ml) and filtered. The precipitate was further washed with 20 ml of anhydrous ethanol and air dried. This product (1.98 g) was dissolved in 50 ml anhydrous methanol and the resulting solution was cooled to 0–5° C. in an ice-water bath under nitrogen. Then sodium methoxide (0.54 g in 6 ml anhydrous methanol under nitrogen) cooled to 5–10° C. was added slowly to the above solution under continuous stirring over a period of 10 min. After an additional 5 min. stirring the mixture was concentrated at 18° C. The resulting solid was dissolved in 100 ml distilled water. The nearly clear filtrate was freeze dried.

What is claimed is:

1. A compound of the formula:

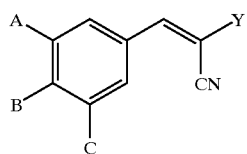

wherein A and C are independently alkyl of 1–6 carbon atoms, hydroxy or alkoxy of 1–6 carbon atoms; B is —$CO_2Z$,—$O(CH_2)_mCO_2Z_2$, —$SO_3Z$ or —$OPO_3Z$, Y is cyano; m is 1 to 4 ; and Z is H, a cation or alkyl of 1–6 carbon atoms.

2. A compound of the formula:

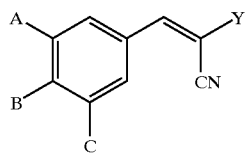

wherein A and C are independently H, alkyl of 1–6 carbon atoms, hydroxy or alkoxy of 1–6 carbon atoms;

B is —$O(CH_2)_mCO_2Z$, —$SO_3Z$ or —$OPO_3Z_2$; Y is cyano; m is 1–4 and Z is H, a cation or alkyl of 1–6 carbon atoms.

3. A compound according to claim 2 wherein A and C are hydrogen.

4. A compound according to claim 2, wherein B is —$OPO_3Z$.

5. A compound according to claim 2, wherein B is —$SO_3Z$.

6. A compound according to claim 2, wherein B is —$O(CH_2)_mCO_2Z$.

7. A compound according to claim 4, wherein Z is H.

8. A compound according to claim 5, wherein Z is Na+.

9. A compound according to claim 6, wherein m=1 and Z is Na+.

10. A compound according to claim 6, wherein m=1 and Z is ethyl.

* * * * *